United States Patent
Hopper

(10) Patent No.: US 10,918,869 B2
(45) Date of Patent: Feb. 16, 2021

(54) METHODS AND SYSTEMS THAT MONITOR AND RESPOND TO CHANGES IN PHYSIOLOGICAL STATUS BASED ON MEASUREMENTS OF RESPIRATION CHARACTERISTICS AND PULMONARY ARTERIAL PRESSURE OBTAINED FROM IMPLANTABLE SENSORS

(71) Applicant: Pacesetter, Inc., Santa Clara, CA (US)

(72) Inventor: Donald Lee Hopper, Maple Grove, MN (US)

(73) Assignee: Pacesetter, Inc., Sylmar, CA (US)

(*) Notice: Subject to any disclaimer, the term of this patent is extended or adjusted under 35 U.S.C. 154(b) by 288 days.

(21) Appl. No.: 15/987,771

(22) Filed: Jun. 15, 2018

(65) Prior Publication Data

US 2019/0381321 A1   Dec. 19, 2019

(51) Int. Cl.
*A61N 1/365* (2006.01)
*A61N 1/39* (2006.01)
*A61N 1/372* (2006.01)
*A61N 1/37* (2006.01)

(52) U.S. Cl.
CPC ..... *A61N 1/36585* (2013.01); *A61N 1/36521* (2013.01); *A61N 1/37258* (2013.01); *A61N 1/3956* (2013.01); *A61N 1/39622* (2017.08); *A61N 1/36542* (2013.01); *A61N 1/36564* (2013.01); *A61N 1/3712* (2013.01); *A61N 1/37223* (2013.01)

(58) Field of Classification Search
CPC .............. A61N 1/36585; A61N 1/3956; A61N 1/39622; A61N 1/37258; A61N 1/36521; A61N 1/36564; A61N 1/36542; A61N 1/3712; A61N 1/37223
See application file for complete search history.

(56) References Cited

U.S. PATENT DOCUMENTS

| | | |
|---|---|---|
| 6,273,856 B1 | 8/2001 | Sun et al. |
| 6,275,727 B1 | 8/2001 | Hopper et al. |
| 6,741,885 B1 | 5/2004 | Park et al. |
| 7,488,290 B1 | 2/2009 | Stahmann et al. |
| 7,599,741 B2 | 10/2009 | Hopper et al. |
| 7,833,164 B2 | 11/2010 | Scheiner et al. |

(Continued)

*Primary Examiner* — Mark Bockelman
(74) *Attorney, Agent, or Firm* — Vierra Magen Marcus LLP

(57) ABSTRACT

Embodiments described herein generally relate to methods and systems for monitoring and responding to changes in a patient's physiologic status. A method includes sensing pulmonary arterial pressure (PAP) and thoracic impedance of a patient at rest. The method also includes detecting, based on the sensed PAP, whenever the patient's PAP at rest is outside an acceptable range of PAP measures for the patient at rest, and detecting, based on the sensed thoracic impedance, whenever the patient's respiration at rest is outside an acceptable range of respiration measures for the patient at rest. Various different actions are triggered depending upon whether the patient's PAP at rest is outside the acceptable range of PAP measures for the patient at rest, and whether the patient's respiration at rest is within the acceptable range of respiration measures for the patient at rest. Other embodiments relate to similar methods performed at other levels of exertion.

23 Claims, 5 Drawing Sheets

(56) References Cited

U.S. PATENT DOCUMENTS

| | | | |
|---|---|---|---|
| 8,145,309 B2* | 3/2012 | Farazi | G16H 40/63 |
| | | | 607/25 |
| 8,615,296 B2 | 12/2013 | Pastore et al. | |
| 8,639,324 B2 | 1/2014 | Elferri et al. | |
| 8,903,491 B2 | 12/2014 | Hopper et al. | |
| 8,954,146 B2 | 2/2015 | Hopper et al. | |
| 9,220,429 B2 | 12/2015 | Nabutovsky et al. | |
| 9,277,885 B2 | 3/2016 | Hopper et al. | |
| 9,757,048 B2 | 9/2017 | Xi et al. | |
| 9,861,817 B2 | 1/2018 | Cho et al. | |
| 2005/0192637 A1* | 9/2005 | Girouard | A61M 5/1723 |
| | | | 607/3 |
| 2008/0221636 A1 | 9/2008 | Pastore et al. | |
| 2011/0046520 A1 | 2/2011 | Fricke et al. | |
| 2014/0343438 A1 | 11/2014 | Sweetney et al. | |
| 2015/0164421 A1 | 6/2015 | Hopper et al. | |

\* cited by examiner

METHODS AND SYSTEMS THAT MONITOR AND RESPOND TO CHANGES IN PHYSIOLOGICAL STATUS BASED ON MEASUREMENTS OF RESPIRATION CHARACTERISTICS AND PULMONARY ARTERIAL PRESSURE OBTAINED FROM IMPLANTABLE SENSORS

FIELD OF TECHNOLOGY

Embodiments described herein generally relate to methods and systems for monitoring and responding to changes in a patient's physiologic status.

BACKGROUND

Change in physiological status of an individual can be determined through various means that include physical examination, physical functional testing, or through invasive or non-invasive testing. Various sensors have been incorporated into implantable medical devices (IMDs) to monitor changes in physiological status, such as lung fluid, cardiac output, heart rate, morphology measures of heart contraction depolarization and repolarization. In addition, implantable sensors that monitor pulmonary arterial pressure (PAP) through monitoring of the right atrium have been developed. Many of these sensors have been utilized in some fashion to provide early detection of heart failure (HF) decompensation in IMDs. Exemplary types of IMDs that may utilize one or more such sensors include implantable pacemakers, implantable cardioverter defibrillator (ICDs), implantable cardiac resynchronization therapy pacemakers (CRT-Ps), and implantable cardiac monitors (ICMs). Additionally, there exist external cardiac monitors (ECMs) that are capable measuring cardiac timing cycles. Despite the existence of IMDs and ECMs that are capable of monitoring changes in physiological status, there still exists a need for improvements in monitoring changes in physiological status and responding thereto.

SUMMARY

Described herein are methods and systems for monitoring and responding to changes in a patient's physiologic status. Certain methods are for use by a system that includes at least a portion of which is implanted within a patient. For example, one or more sensors of the system can be implanted. Such a method can include using a first implantable sensor to determine a baseline measure of pulmonary arterial pressure (PAP) for the patient at rest, and using a second implantable sensor to determine a baseline measure of respiration for the patient at rest. In certain embodiments, the first implantable sensor is configured to sense PAP, and the second implantable sensor is configured to sense thoracic impedance. More specifically, the second implantable sensor can be configured to produce a thoracic impedance signal from which one or more types of respiration measures can be determined.

The method can also include determining an acceptable range of PAP measures for the patient at rest based on the baseline measure of PAP that is determined for the patient at rest, and determining an acceptable range of respiration measures for the patient at rest based on the baseline measure of respiration that is determined for the patient at rest. Additionally, the method can include using the first implantable sensor to detect whenever the patient's PAP at rest is outside the acceptable range of PAP measures for the patient at rest, and using the second implantable sensor to detect whenever the patient's respiration at rest is outside the acceptable range of respiration measures for the patient at rest. A first action is triggered in response to detecting that the patient's PAP at rest is outside the acceptable range of PAP measures for the patient at rest, while contemporaneously the patient's respiration at rest is within the acceptable range of respiration measures for the patient at rest. A second action is triggered in response to detecting that the patient's respiration at rest is outside the acceptable range of respiration measures for the patient at rest, while contemporaneously the patient's PAP at rest is within the acceptable range of PAP measures for the patient at rest. A third action is triggered in response to detecting that the patient's PAP at rest is outside the acceptable range of PAP measures for the patient at rest, while contemporaneously the patient's respiration at rest is outside the acceptable range of respiration measures for the patient at rest. The first, second, and third actions differ from one another.

In accordance with certain embodiments, the first action that is triggered is a first alert that informs at least one of the patient or a medical personnel that the patient's PAP is abnormal for the patient; the second action that is triggered is a second alert that informs at least one of the patient or a medical personnel that the patient's respiration is abnormal for the patient; and the third action that is triggered is a third alert that informs at least one of the patient or a medical personnel that both the patient's PAP is abnormal for the patient and the patient's respiration is abnormal for the patient. The third action that is triggered can additionally, or alternatively, involve adjusting at least one pacing parameter that is used to deliver cardiac pacing therapy using a portion of the system that is implanted.

In accordance with certain embodiments, the baseline measure of respiration for the patient at rest can be selected from the group consisting of: a baseline measure indicative of respiration rate for the patient at rest; a baseline measure indicative of tidal volume for the patient at rest; a baseline measure indicative of inspiratory time for the patient at rest; a baseline measure indicative of expiratory time for the patient at rest; a baseline measure indicative of minute ventilation for the patient at rest; and a baseline measure indicative of morphology of a signal waveform indicative of respiration for the patient at rest.

In accordance with certain embodiments, the second implantable sensor is used to determine a separate baseline measure of respiration for the patient at rest for each of a plurality of different types of measures of respiration, and an acceptable range of respiration measures for the patient at rest is determined for each of the plurality of different types of measures of respiration based on the respective baseline measure of respiration that is determined for the patient at rest. In such embodiments, the patient's respiration at rest can be determined to be outside the acceptable range of respiration measures for the patient at rest whenever N out of M of the different types of measures of respiration is/are outside their respective baseline measure of respiration for the patient at rest, where M is a number specifying the different types of measures of respiration for which a respective acceptable range of respiration measures is determined for the patient at rest, and N is a predefined number that is equal to or less than M. In such embodiments, an acceptable range of respiration measures for the patient at rest can be determined for at least two of the following different types of measures of respiration: respiration rate for the patient at rest; tidal volume for the patient at rest; inspiratory time for the patient at rest; expiratory time for the patient at rest;

minute ventilation for the patient at rest; or morphology of a signal waveform indicative of respiration for the patient at rest. In accordance with certain embodiments, a method also includes using an implantable sensor, which may or may not be the same as one of the first or second implantable sensors, to determine when the patient is at rest. For example, the implantable sensor that is used to determine when the patient is at rest can be an accelerometer, which is different than the first and second implantable sensors.

In accordance with certain embodiments, a system, at least a portion of which is implantable within a patient, includes first and second implantable sensor and one or more processors. One or more such processors can be implanted, and/or one or more such processors can be part of an external device or system. The first implantable sensor is configured to sense pulmonary arterial pressure PAP, and the second implantable sensor is configured to sense thoracic impedance. The one or more processors is/are configured to use the first implantable sensor to determine a baseline measure of PAP for the patient at rest, and use the second implantable sensor to determine a baseline measure of respiration for the patient at rest. The one or more processor is/are also configured to determine an acceptable range of PAP measures for the patient at rest based on the baseline measure of PAP that is determined for the patient at rest, and determine an acceptable range of respiration measures for the patient at rest based on the baseline measure of respiration that is determined for the patient at rest. Additionally, the one or more processors is/are configured to use the first implantable sensor to detect whenever the patient's PAP at rest is outside the acceptable range of PAP measures for the patient at rest, and use the second implantable sensor to detect whenever the patient's respiration at rest is outside the acceptable range of respiration measures for the patient at rest. Further, the one or more processors is/are configured to trigger a first action, a second action, and a third action. The first action is triggered in response to detecting that the patient's PAP at rest is outside the acceptable range of PAP measures for the patient at rest, while contemporaneously the patient's respiration at rest is within the acceptable range of respiration measures for the patient at rest. The second action is triggered in response to detecting that the patient's respiration at rest is outside the acceptable range of respiration measures for the patient at rest, while contemporaneously the patient's PAP at rest is within the acceptable range of PAP measures for the patient at rest. The third action is triggered in response to detecting that the patient's PAP at rest is outside the acceptable range of PAP measures for the patient at rest, while contemporaneously the patient's respiration at rest is outside the acceptable range of respiration measures for the patient at rest. The first, second, and third actions differ from one another.

In accordance with certain embodiments, the first action that is triggered is a first alert that informs at least one of the patient or a medical personnel that the patient's PAP is abnormal for the patient; the second action that is triggered is a second alert that informs at least one of the patient or a medical personnel that the patient's respiration is abnormal for the patient; and the third action that is triggered is a third alert that informs at least one of the patient or a medical personnel that both the patient's PAP is abnormal for the patient and the patient's respiration is abnormal for the patient. The third action that is triggered can additionally, or alternatively, involve adjusting at least one pacing parameter that is used to deliver cardiac pacing therapy using a portion of the system that is implanted.

Other embodiments relate to similar methods performed at other levels of exertion, in addition to or instead of when the patient is at rest. Other embodiments also relate to similar systems that can be used when the patient is at other levels of exertion, in addition to or instead of when the patient is at rest.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1:
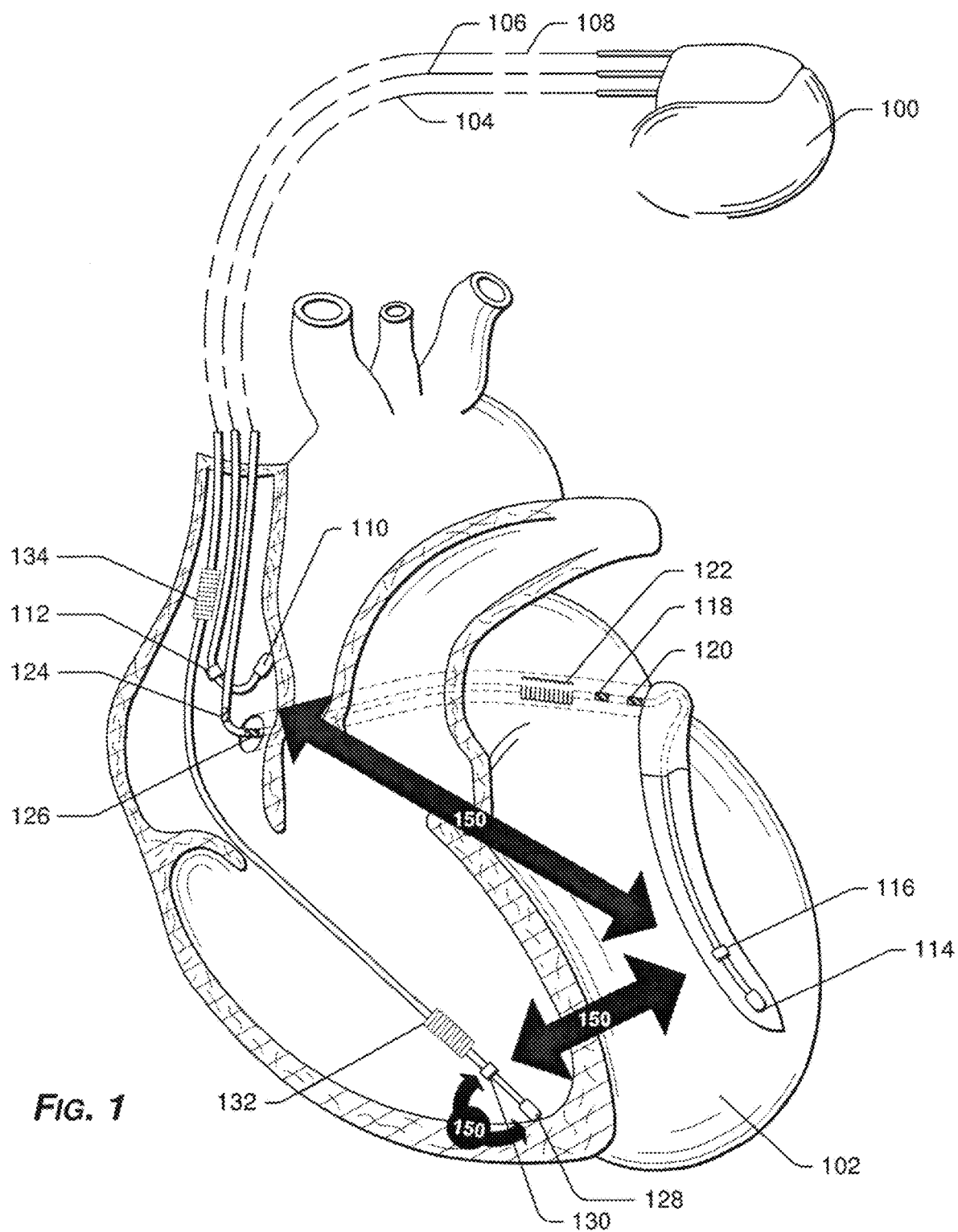
FIG. 1 illustrates an exemplary implantable medical device in electrical communication with a patient's heart.

Certain embodiments of the present technology described herein relate to methods and systems that monitor changes in a patient's physiological status and respond thereto. More specifically, in certain such embodiments utilize a combination of measurements of pulmonary arterial pressure (PAP) and one or more characteristics of respiration to provide an accurate detection of the type and severity of cardiopulmonary distress that a patient may be experiencing. Types of cardiopulmonary distress that can be monitored for and responded to using embodiments of the present technology include dyspnea, orthopnea, and paroxysmal nocturnal dyspnea, but are not limited thereto. Dyspnea is disordered or inadequate breathing, which results in shortness of breath. Orthopnea, which is also known as or orthopnoea, is shortness of breath (i.e., dyspnea) that occurs or increases when a person lies down (i.e., is in a supine position). People with orthopnea typically need to sleep in an upright position, e.g., propped up in bed or sitting in a chair. Paroxysmal nocturnal dyspnea (PND), which is also known as paroxysmal nocturnal dyspnoea, refers to attacks of severe shortness of breath and coughing that generally occur at night. PND usually awakens a person from sleep and may be quite frightening.

By utilizing a combination of measurements of PAP and respiration, embodiments of the present technology can provide for early detection of cardiopulmonary distress and increases thereof, which can be used for triggering changes in therapy by medical personal and/or automatic changes of pacing therapy by a pacemaker or other IMD. Additionally, or alternatively, in accordance certain embodiments, a detection of cardiopulmonary distress or an increase thereof can trigger an alert to a patient and/or to medical personal via established wireless communication.

Transthoracic impedance measurements, which are measurements of the changing impedance in a patient's thoracic cavity, can be used to monitor various different types of respiratory characteristics of the patient, such as respiration rate, tidal volume, inspiratory time, expiratory time, and minute ventilation. Generally, transthoracic impedance increases as a patient inhales and decreases as the patient exhales. A circuit designed to detect this impedance variation, based on impedance pneumography, can deliver a high frequency differential current driven onto the patient through a pair of electrodes. The impedance variation caused by breathing results in a corresponding voltage change that can be measured on the same electrodes (e.g., using a 2-wire respiration measurement), or on a different pair of electrodes (e.g., using a 4-wire respiration measurement). Transthoracic impedance technologies have been well established and used for patient monitoring and for pacing therapies, e.g., for rate adaptive pacing therapy. However, measures of transthoracic impedance alone may not sufficiently reveal changes in a patient's physiological status to which an appropriate response should be performed. The term transthoracic impedance is also referred to more succinctly herein as thoracic impedance.

Pulmonary arterial pressure (PAP) is a measure of the blood pressure found in the main pulmonary artery. PAP can be measured, for example, by implanting a PAP sensor into a patient's pulmonary artery. One exemplary implantable PAP sensor is the CardioMEMS™ PA Sensor, which is available from Abbott Laboratories (headquartered in Lake Bluff, Ill., USA), which sensor is part of Abbott's FDA approved CardioMEMS™ HF System. As described by U.S. Pat. No. 7,699,059 entitled "Implantable Wireless Sensor" and U.S. Pat. No. 7,679,355 entitled "Communicating with an Implanted Wireless Sensor," these sensors are MEMS-based sensors that are implanted in the pulmonary artery, more particularly in the distal pulmonary artery branch, and are configured to be energized with RF energy to return high-frequency, high-fidelity dynamic pressure information from a precisely-selected location within a patient's body. The mean PAP of a person is typically within the range of 9-18 mmHg inclusively. PAP that is greater than 25 mmHg at rest, or greater than 30 mmHg during exercise, is classified as pulmonary hypertension.

Exemplary Implantable Medical Device

Before providing additional details of specific embodiments of the present technology, an exemplary implantable medical device (IMD) that can be used to implement embodiments of the present technology, will first be described with reference to FIGS. 1 and 2.

As shown in FIG. 1, an exemplary implantable medical device ("implantable device" 100), in this case an exemplary implantable cardioverter-defibrillator (ICD), is in electrical communication with a patient's heart 102 by way of three leads, 104, 106 and 108, suitable for sensing, delivering multi-chamber stimulation and shock therapy. Not every configuration has all of the illustrated electrodes, but a given actual configuration may include some of the illustrated electrodes and/or even more electrodes than illustrated. The implantable device 100 can also be referred to herein as IMD 100.

To sense atrial cardiac signals and to provide right atrial chamber stimulation therapy, the implantable device 100 is coupled to an implantable right atrial lead 106, typically having an atrial tip electrode 110 and an atrial ring electrode 112, which typically is implanted in the patient's right atrial appendage. Implantable device 100 is also known as and referred to as a pacing device, a pacing apparatus, a cardiac rhythm management device, or an implantable cardiac stimulation device. Alternatively, the implantable device 100 could be a defibrillator, or cardioverter, or have combined pacing and defibrillation/cardioversion capabilities.

To sense left atrial and ventricular cardiac signals and to provide left chamber pacing therapy, the implantable device 100 is coupled to a "coronary sinus" lead 104 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 104 is designed to receive atrial and ventricular cardiac signals and to deliver left ventricular pacing therapy using a LV tip electrode 114 and a LV ring electrode 116. Left atrial pacing therapy uses, for example, first and second left atrial (LA) ring electrodes 118 and 120. Shocking therapy can be performed using at least a left atrial (LA) coil electrode 122. For a description of an exemplary coronary sinus lead, see U.S. Pat. No. 7,313,444 (Pianca et al.) entitled "A Self-Anchoring Coronary Sinus Lead" and U.S. Pat. No. 5,466,254 (Helland) entitled "Coronary Sinus Lead with Atrial Sensing Capability," which patent documents are incorporated herein by reference. Coronary sinus lead 104 may also include a pair of right atrial (RA) ring electrodes 124 and 126, which may be used to provide right atrial chamber pacing therapy.

The implantable device 100 is also shown in electrical communication with the patient's heart 102 by way of an implantable right ventricular lead 108, typically having an right ventricular (RV) tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

A multi-vector network 150 can obtain impedance measurements over multiple vectors simultaneously, quasi-simultaneously, or sequentially using any of the electrodes illustrated in FIG. 1, either in pairs or in combinations of three or more electrodes. For the sake of illustration, an exemplary multi-vector network 150 is shown in FIG. 1. Although the illustrated multi-vector network 150 includes three vectors, other exemplary multi-vector networks 150 may include more (or less) than three vectors. The illustrated multi-vector network 150 includes three intracardiac vectors: a vector between the LV chamber and the RA chamber, a vector between the LV chamber and the RV chamber, and a vector between two electrodes in the RV chamber.

The term "multi-vector network 150" will be used herein to refer to any multi-vector network with two or more vectors between physical, logical, and or virtual electrodes, such as between the physical electrodes illustrated in FIG. 1. In the description below, "multi-vector network 150" sometimes includes at least one intracardiac vector—a vector confined to within cardiac tissue, or within the pericardial sac.

Figure 2:
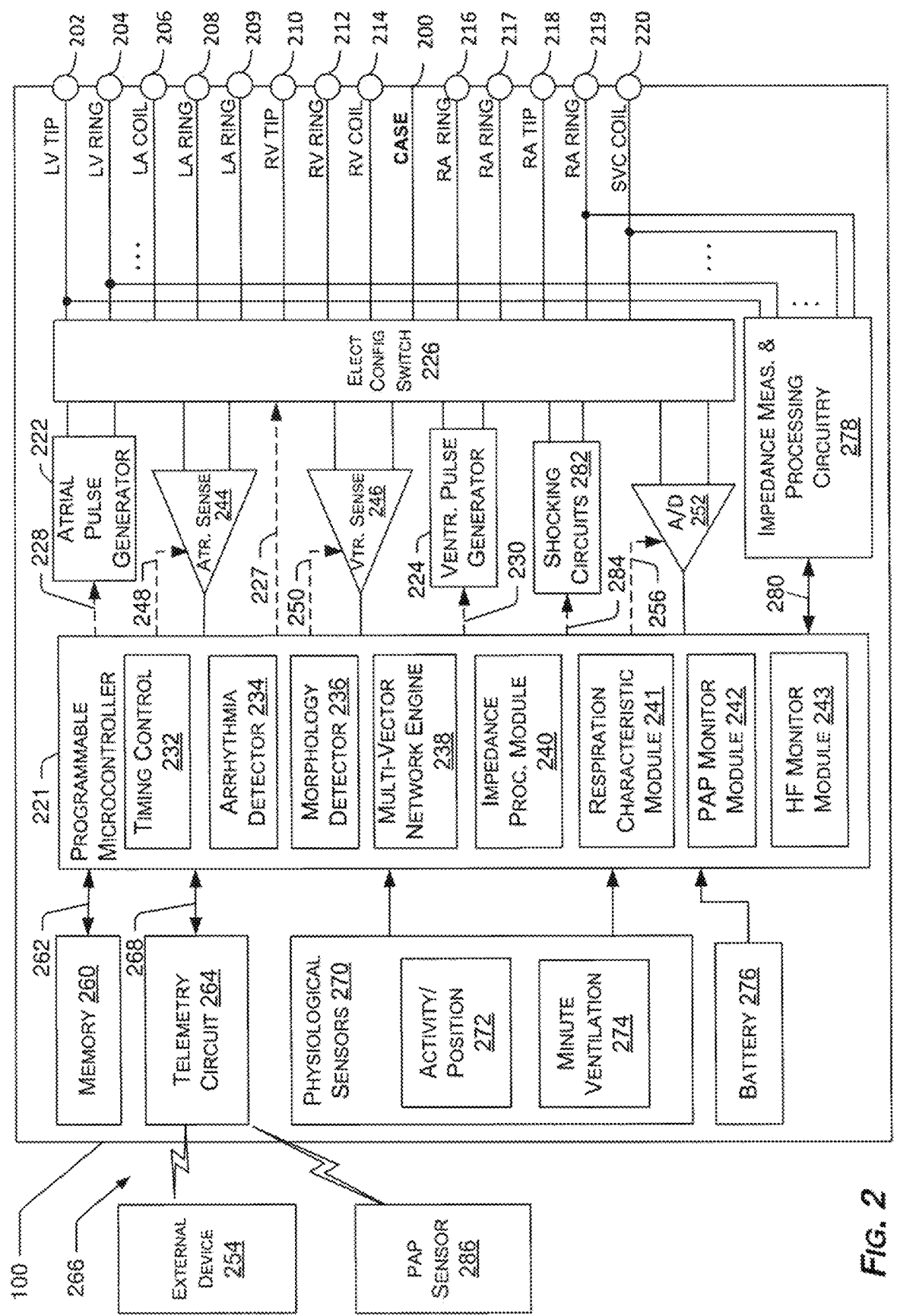
FIG. 2 is a block diagram depicting various components of the exemplary implantable medical device of FIG. 1, according to an embodiment.

FIG. 2 shows an exemplary block diagram depicting various components of the exemplary implantable device 100. The components are typically contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 122, 132, 134 for stimulating purposes. The case 200 further includes a connector (not shown) having a plurality of terminals (202, 204, 206, 208, 209, 210, 212, 214, 216, 217, 218, 219, and 220—shown schematically with the names of the electrodes to which they are connected shown next to the terminals), including:
  a left ventricular tip terminal (LV TIP) 202 for left ventricular tip electrode 114;
  a left ventricular ring terminal (LV RING) 204 for left ventricular ring electrode 116;
  a left atrial shocking terminal (LA COIL) 206 for left atrial coil electrode 122;
  a left atrial ring terminal (LA RING) 208 for left atrial ring electrode 118;
  a left atrial ring terminal (LA RING) 209 for left atrial ring electrode 120;
  a right ventricular tip terminal (RV TIP) 210 for right ventricular tip electrode 128;
  a right ventricular ring terminal (RV RING) 212 for right ventricular ring electrode 130;
  a right ventricular shocking terminal (RV COIL) 214 for RV coil electrode 132;
  a right atrial ring terminal (RA RING) 216 for atrial ring electrode 124;
  a right atrial ring terminal (RA RING) 217 for right atrial ring electrode 126;
  a right atrial tip terminal (RA TIP) 218 for atrial tip electrode 110;
  a right atrial ring terminal (RA RING) 219 for atrial ring electrode 112; and
  a SVC shocking terminal (SVC COIL) 220 for right atrial SVC coil electrode 134.

The exemplary implantable device 100 may include a programmable microcontroller 221 that controls various operations of the implantable device 100, including cardiovascular monitoring, hemodynamic monitoring, and cardiovascular stimulation therapy. In accordance with certain embodiments of the present technology, the microcontroller 221 can also be used to monitor PAP and monitor one or more respiration characteristics and triggered actions based on such monitoring. The microcontroller 221 can include a microprocessor (or equivalent control circuitry), RAM and/or ROM memory, logic and timing circuitry, state machine circuitry, and/or I/O circuitry, but is not limited thereto.

The exemplary implantable device 100 may further include an atrial pulse generator 222 and a ventricular pulse generator 224 that generate pacing stimulation pulses for delivery by the right atrial lead 106, the coronary sinus lead 104, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 221, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 221 via appropriate control signals 228 and 230, respectively, to trigger or inhibit the stimulation pulses.

Microcontroller 221 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 221 may also implement an arrhythmia detector 234, a morphology detector 236, a multi-vector network engine 238, an impedance processing module 240, a respiration characteristic module 241, a PAP monitor module 242, and a heart failure (HF) module 243. The microcontroller 221 may process input from physiological sensors 270, such as accelerometers of an activity/position module 272, and a minute ventilation module 274, etc.

Figure 6:
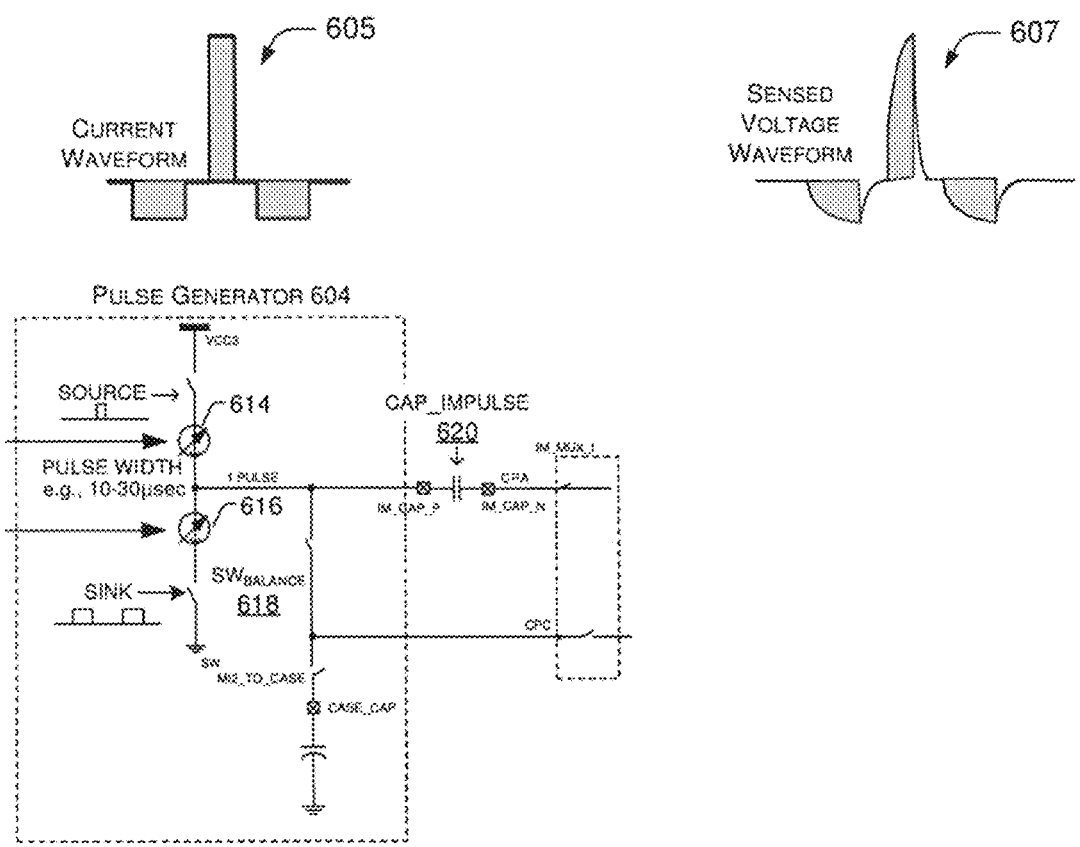
FIG. 6 illustrates exemplary details of a current pulse generator that can be used to obtain a thoracic impedance signal, and an exemplary multiphasic current pulse waveform generated by the current pulse generator and corresponding sensed voltage waveform.

The respiration characteristic module 241 can detect one or more characteristics of respiration including, but not limited to, breath by breath and/or summations of respiration rate, tidal volume, inspiratory time, expiratory time, and/or minute ventilation. Such characteristics can be determined from a thoracic impedance signal obtained using impedance measurement and processing circuitry 278, but are not limited thereto. For example, a thoracic impedance signal can be obtained by applying a low-level electrical current from a pulse generator (e.g., 222 or 224 in FIG. 2, or 604 in FIG. 6) to a ring electrode (e.g., 112, 116, 18, 124, 126, or 113) of a pacing lead (e.g., 104, 106, or 108) and measuring a resulting voltage between a tip electrode (e.g., 110, 114, or 128) of the pacing lead back to a case electrode (e.g., 200) of the implantable device (e.g., 100). This is just one exemplary way in which an implantable device (e.g., 100) can obtain a thoracic impedance signal. The use of other electrodes and/or other techniques for obtaining a thoracic impedance signal are also within the scope of the embodiments described herein. FIG. 6, discussed below, provides exemplary details of a pulse generator that can be used to applying a low-level electrical current that can be used to obtain a thoracic impedance signal.

In accordance with certain embodiments of the present technology, the respiration characteristic module 241 can detect one or more such characteristics of respiration when a patient is at rest in order to determine and save baseline measures of such characteristics of respiration. Such measures can be raw measures, or they can be normalized measured. For example, the baseline measure indicative of inspiratory time for a patient at rest can be a raw measure of inspiration, or a normalized measure that is determined by dividing the raw measure of inspiration by the total respiration cycle time. The implantable device 100 can determine when a patient is at rest based on measurements obtained using the activity/posture sensor 272, and more specifically, using an accelerometer. The implantable device 100 can alternative determine when a patient is at rest using the minute ventilation sensor 274. For example, a short term average minute ventilation value can be determined and compared to a long term average or baseline minute ventilation value, and when the difference between the short and long term averages is below a specified threshold that can be interpreted as or used as an indication that the patient is at rest.

The PAP monitor module 242 can obtain measures of pulmonary arterial pressure (PAP) from an implanted PAP sensor 286 that is in communication with the PAP monitor module 242, or more generally, the implantable device 100. As mentioned above, one exemplary implantable PAP sensor is the CardioMEMS™ PA Sensor, which is available from Abbott Laboratories (headquartered in Lake Bluff, Ill., USA), which sensor is part of Abbott's FDA approved CardioMEMS™ HF System. The PAP sensor 286 can, for example, be implanted within a patient's pulmonary artery in order to obtain measures of PAP, and can provide such measures to the PAP monitor module 242, or more generally, the implantable device 100, using wireless communication. For example, as described by U.S. Pat. No. 7,699,059 entitled "Implantable Wireless Sensor" and U.S. Pat. No. 7,679,355 entitled "Communicating with an Implanted Wireless Sensor," such a MEMS-based sensor can be implanted in the pulmonary artery, and more particularly in the distal pulmonary artery branch, and can be configured to be energized with RF energy to return high-frequency, high-fidelity dynamic pressure information from a precisely-selected location within a patient's body. Other types of communication between the PAP sensor 286 and the implantable device 100 are also possible, including wired communication, or conductive communication, but is not limited thereto. In accordance with certain embodiments, the telemetry circuit 264 of the device can wirelessly communicate with the PAP sensor 286.

In accordance with certain embodiments, the HF module 243 can determine an acceptable range of PAP measures for the patient at rest based on the baseline measure of PAP that is determined for the patient at rest. The HF module 243 can also determine an acceptable range of respiration measures for the patient at rest based on the baseline measure of respiration that is determined for the patient at rest. It would also be possible for an external device 254 to determine such acceptable ranges and provide such information to the implantable device 100 via a wireless communication link between the external device 254 and the implantable device 100. The HF module 243 can also determine when a patient's PAP at rest is outside the acceptable range of PAP measures for the patient at rest, determine when a patient's respiration at rest is outside the acceptable range of respiration measures for the patient at rest, and trigger various different actions in response to such determinations, as will be described in additional detail below.

It would also be possible for the external device 254 make such determination and/or trigger various different actions in response to such determinations. More generally, the external device 254 can perform one or more of the above described determinations that were described as being performed by the respiration characteristic module 241, the PAP monitor module 242, and/or the HF monitor module 243. The external device 254 can include telemetry circuitry and one or more processors, and can perform such determinations using its processor(s). It is also possible that the external device 254 communicate with a central processing system, via telephone landlines, broadband service, or a wireless network, and that the central processing system can perform at least a portion of the determinations, or more generally, at least some patient monitoring. The external device 254 can be, e.g., a Merlin@home™ transmitter, which is available from Abbott Laboratories (headquartered in Lake Bluff, Ill., USA), but is not limited thereto. The central processing system can, e.g., be part of the Merlin-.net™ Patient Care Network (PCN), which is supported by Abbott Laboratories, but is not limited thereto.

The components 234, 236, 238, 240, 241, 242, 243 may be implemented in hardware as part of the microcontroller 221, or as software/firmware instructions programmed into an implementation of the implantable device 100 and executed on the microcontroller 221 during certain modes of operation. Although not shown, the microcontroller 221 may further include other dedicated circuitry and/or firmware/software components that assist in monitoring various conditions of the patient's heart and lungs and managing pacing therapies.

Atrial sensing circuits 244 and ventricular sensing circuits 246 may also be selectively coupled to the right atrial lead 106, coronary sinus lead 104, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary implantable device 100 to sense low amplitude signal characteristics of atrial or ventricular fibrillation.

The outputs of the atrial and ventricular sensing circuits 244 and 246 are connected to the microcontroller 221 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 221 over signal lines 248 and 250 to control, for example, the gain and the timing of blocking circuitry (not shown) optionally coupled to the inputs of the sensing circuits 244, 246.

Cardiac signals, including signals involved in impedance measurements, are supplied to an analog-to-digital (ND) data acquisition system 252, which is configured to acquire these signals, convert the raw analog data into a digital signal, and store the digital signals for later processing and/or telemetric transmission to an external device 254. The data acquisition system 252 is coupled to the right atrial lead 106, the coronary sinus lead 104, and the right ventricular lead 108 through the switch 226 to process signals across any pair of desired electrodes.

The data acquisition system 252 is coupled to the microcontroller 221, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 221 detects a depolarization signal during a window following a stimulation pulse, the presence of which indicates that capture has occurred. The microcontroller 221 enables capture detection by triggering the ventricular pulse generator 224 to generate a stimulation pulse, starting a capture detection window using the timing control circuitry 232 within the microcontroller 221, and enabling the data acquisition system 252 via control signal 256 to sample the cardiac signal that falls in the capture detection window and, based on the amplitude, determines if capture has occurred.

The microcontroller 221 is further coupled to a memory 260 by a suitable data/address bus 262. The programmable operating parameters used by the microcontroller 221 are stored in memory 260 and used to customize the operation of the exemplary implantable device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 102 within each respective tier of therapy. The memory 260 can also store various different types of baseline measures, as well as acceptable ranges of various different types of measures, examples of which are discussed below.

The operating parameters of the exemplary implantable device 100 may be non-invasively programmed into the memory 260 through a telemetry circuit 264 in telemetric communication via communication link 266 with the external device 254, such as a programmer, local transceiver, or a diagnostic system analyzer. The microcontroller 221 can activate the telemetry circuit 264 with a control signal 268. The telemetry circuit 264 allows intracardiac electrograms and status information relating to the operation of the exemplary implantable device 100 (as contained in the microcontroller 221 or memory 260) to be sent to the external device 254 through an established communication link 266.

The physiological sensors 270 referred to above can further include, for example, "rate-responsive" sensors that adjust pacing stimulation rates according to the exercise state of the patient. Accordingly, the microcontroller 221 responds by adjusting the various pacing parameters (such as rate, etc.) at which the atrial and ventricular pulse generators 222 and 224 generate stimulation pulses.

The physiological sensors 270 may include mechanisms and sensors to detect bodily movement, minute ventilation, changes in blood pressure, changes in cardiac output, changes in the physiological condition of the heart, diurnal changes in activity (e.g., detecting sleep and wake states), G-force acceleration of the ICD case 200, length of the cardiac QT interval, blood oxygen saturation, blood pH, changes in temperature, respiration rate, and QRS wave duration. While shown as being included within the exemplary implantable device 100, the physiological sensor(s) 270 may also be external to the exemplary implantable device 100, yet still be implanted within or carried by the patient, e.g., a blood pressure probe. Examples of physiological sensors external to the case 200 that may be deployed by implantable device 100 include sensors that, for example, sense respiration activities, 02 saturation, evoked response, pH of blood, and so forth.

The illustrated physiological sensors 270 include one or more activity/position sensors 272 (e.g., 1D or 3D accelerometers, movement sensors, etc.) to detect changes in the patient's position. The activity/position sensors 272 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, an accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 274 may also be included in the physiological sensors 270 in order to sense rate and depth of breathing. Minute ventilation can be measured as the total volume of air that moves in and out of a patient's lungs in a minute. The MV sensor 274 may use impedance measurement and processing circuitry 278 to sense air movement by measuring impedance across the chest cavity.

The impedance measurement and processing circuitry 278 can communicate with the microcontroller 221, e.g., via control signals 280 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measurement and processing circuitry 278 is shown as being connected to each of the terminals 202, 204, 206, 208, 209, 210, 212, 214, 216, 217, 218, 219 and 220. Through use of switching circuitry the impedance measurement and processing circuitry 278 can be connected to any desired electrode combinations, and networks of vectors can be selected by the multi-vector network engine 238.

The exemplary implantable device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 10 A, at voltages above 500 V, for periods of 2-20 microseconds). The battery 276 also desirably has predictable discharge characteristics so that elective replacement time can be detected. As one example, the exemplary implantable device 100 employs lithium/silver vanadium oxide batteries.

The exemplary implantable device 100 can further include magnet detection circuitry (not shown), coupled to the microcontroller 221, to detect when a magnet is placed over the exemplary implantable device 100. A magnet may be used by a clinician to perform various test functions of the exemplary implantable device 100 and/or to signal the microcontroller 221 that an external programmer (e.g., 254) is in place to receive or transmit data to the microcontroller 221 through the telemetry circuits 264.

The microcontroller 221 further controls a shocking circuit 282 via a control signal 284. The shocking circuit 282 generates shocking pulses of low (e.g., up to 0.5 joules), moderate (e.g., 0.5-10 joules), or high energy (e.g., 11-40 joules), as selected by the microcontroller 221. Such shocking pulses are applied to the patient's heart 102 through at least two shocking electrodes selected, for example, from the left atrial coil electrode 122, the RV coil electrode 132, and/or the SVC coil electrode 134. As noted above, the case 200 may act as an active electrode in combination with the RV coil electrode 132, or as part of a split electrical vector using the SVC coil electrode 134 or the left atrial coil electrode 122 (i.e., using the RV coil electrode 132 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 221 is capable of controlling the synchronous or asynchronous delivery of the shocking pulses.

More generally, the exemplary implantable device 100 can be programmed to stimulate different sets of vascular and cardiac muscles through the same lead/electrode system. The exemplary implantable device 100 can be programmed to vary the output voltage of various pulses to effectively stimulate different muscles of the heart and blood vessels, even though the physical placement of leads and electrodes does not change.

Figure 3:
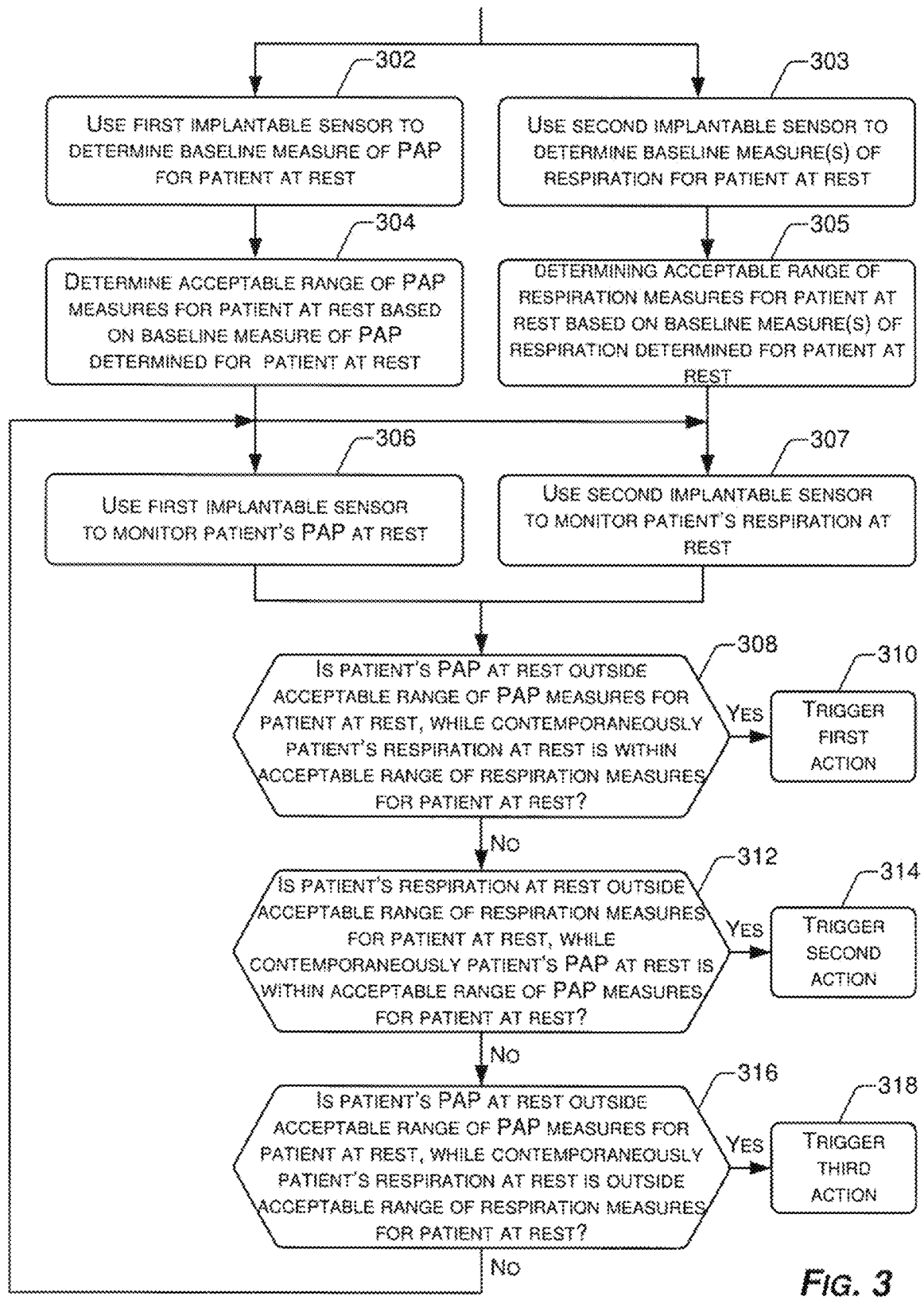
FIG. 3 is a high level flow diagram that is used to summarize methods according to various embodiments of the present technology.

The high level flow diagram of FIG. 3 will now be used to summarize methods according to various embodiments of the present technology. Such methods can be for use by a system, at least a portion of which is implanted in a patient. For example, such methods can be used with a system that includes the implantable device 100 described above with reference to FIGS. 1 and 2, and the implantable PAP sensor 286 described above with reference to FIG. 2. The system with which such methods are used can also include the external device 254, described above with reference to FIG. 2.

Referring to FIG. 3, step 302 involves using a first implantable sensor to determine a baseline measure of pulmonary arterial pressure (PAP) for the patient at rest. Step 303 involves using a second implantable sensor to determine one or more baseline measure(s) of respiration for the patient at rest. The first implantable sensor used at step 302 can be configured to sense PAP, and more specifically can be, e.g., the PAP sensor 286 discussed above with reference to FIG. 2. The second implantable sensor used at step 304 can be configured to sense thoracic impedance, and more specifically can be, e.g., one or more electrodes on an implantable lead and/or the case electrode 200 of an implantable device 100 discussed above with reference to FIGS. 1 and 2. One or more types of respiration measures can be determined from a thoracic impedance signal that is obtained using the second implantable sensor. An activity sensor, such as the sensor 272 discussed above with reference to FIG. 2, can be used to determine when the patient is at rest.

The baseline measure(s) of respiration for the patient at rest, which are determined at step 303 using the second implantable sensor, can include one or more of the following: a baseline measure indicative of respiration rate for the patient at rest; a baseline measure indicative of tidal volume for the patient at rest; a baseline measure indicative of inspiratory time for the patient at rest; a baseline measure indicative of expiratory time for the patient at rest; a baseline measure indicative of minute ventilation for the patient at rest; and a baseline measure indicative of morphology of a signal waveform indicative of respiration for the patient at rest. These measures can be raw measures, or they can be normalized measured. For example, the baseline measure indicative of inspiratory time for the patient at rest can be a raw measure of inspiration, or a normalized measure that is determined by dividing the raw measure of inspiration by the total respiration cycle time.

Still referring to FIG. 3, step 304 involves determining an acceptable range of PAP measures for the patient at rest based on the baseline measure of PAP that is determined for the patient at rest. Step 305 involves determining an acceptable range of respiration measures for the patient at rest based on the baseline measure of respiration that is determined for the patient at rest.

In accordance with certain embodiments, at step 305, an acceptable range of respiration measures for the patient at rest is determined for at least two of the following different types of measures of respiration: respiration rate for the patient at rest; tidal volume for the patient at rest; inspiratory time for the patient at rest; expiratory time for the patient at rest; minute ventilation for the patient at rest; or morphology of a signal waveform indicative of respiration for the patient at rest.

There are various different manners in which the acceptable range of measures of a specific type of measure for the patient at rest, such as PAP and/or respirations measures, can be determined for the patient at rest based on the respective baseline measure. For example, assume that a baseline measure of PAP for the patient at rest is 15 mm Hg. The acceptable range of PAP measures for the patient at rest can simply be defined as any measure of PAP for the patent at rest that is below a threshold determined based on the baseline measure, wherein the threshold can be equal to the baseline measure (i.e., 15 mm Hg) plus a fixed offset (e.g., 5 mm Hg) or plus a specified percentage (e.g., 33%) of the baseline measure. For another example, the acceptable range of PAP measures for the patient at rest can be defined as any measure of PAP for the patent at rest that is within +/−5 mm Hg of the baseline measure, or within +/−33% of the baseline measure. For a further example, assume that a baseline measure of respiration rate (RR) for the patient at rest is 16 breaths per minute (bpm). The acceptable range of RR measures for the patient at rest can simply be defined as any measure of RR for the patent at rest that is below a threshold determined based on the baseline measure, wherein the threshold can be equal to the baseline measure (i.e., 16 bpm) plus a fixed offset (e.g., 4 bpm) or plus a specified percentage (e.g., 25%) of the baseline measure. For still another example, the acceptable range of RR measures for the patient at rest can be defined as any measure of RR for the patent at rest that is within +/−4 bpm of the baseline measure, or within +/−25% of the baseline measure. These are just a few examples of how the acceptable range of measures of a specific type of measure for the patient at rest may be determined, which examples are not intended to be all encompassing. Where a respiration measure is the morphology of a thoracic impedance signal while the patient is at rest, the acceptable range of measures can be specified in terms of an acceptable cross-correlation or other indication of morphology similarity. For example, a thoracic impedance signal can be within an acceptable range where its cross-correlation with a morphological template is within a specified cross-correlation range or threshold. One of ordinary skill in the art reading this description would appreciate that there are various other ways in which to determine the acceptable range of measures of a specific type of measure for the patient at rest, which various other ways are also within the scope of the embodiments described herein. Further, the exemplary offsets and percentages mentioned above are not intended to be limiting, but rather, are just exemplary offsets and percentages.

Still referring to FIG. 3, step 306 involves using the first implantable sensor to monitor the patient's PAP, which can more specifically involve using the first implantable sensor to detect whenever the patient's PAP at rest is outside the acceptable range of PAP measures for the patient at rest. Step 307 involves using the second implantable sensor to monitor the patient's respiration, which can more specifically involves using the second implantable sensor to detect whenever the patient's respiration at rest is outside the acceptable range of respiration measures for the patient at rest.

At step 308 there is a determination of whether the patient's PAP at rest is outside the acceptable range of PAP measures for the patient at rest, while contemporaneously the patient's respiration at rest is within the acceptable range of respiration measures for the patient at rest. If the answer to the determination at step 308 is yes, then a first action is triggered at step 310. In other words, at step 308 and 310 a first action is triggered in response to detecting that the patient's PAP at rest is outside the acceptable range of PAP measures for the patient at rest, while contemporaneously the patient's respiration at rest is within the acceptable range of respiration measures for the patient at rest. If the answer to the determination at step 308 is no, then flow goes to step 312.

At step 312 there is a determination of whether the patient's respiration at rest is outside the acceptable range of respiration measures for the patient at rest, while contemporaneously the patient's PAP at rest is within the acceptable range of PAP measures for the patient at rest. If the answer to the determination at step 312 is yes, then a second action is triggered at step 314, wherein the second action differs from the first action. In other words, at step 312 and 314 a second action is triggered in response to detecting that the patient's respiration at rest is outside the acceptable range of respiration measures for the patient at rest, while contemporaneously the patient's PAP at rest is within the acceptable range of PAP measures for the patient at rest. If the answer to the determination at step 312 is no, then flow goes to step 314.

At step 316 there is a determination of whether patient's PAP at rest is outside the acceptable range of PAP measures for the patient at rest, while contemporaneously the patient's respiration at rest is outside the acceptable range of respiration measures for the patient at rest. If the answer to the determination at step 316 is yes, then a third action is triggered at step 318, wherein the third action differs from the first and second actions. In other words, at step 316 and 318 a third action is triggered in response to detecting that the patient's PAP at rest is outside the acceptable range of PAP measures for the patient at rest, while contemporaneously the patient's respiration at rest is outside the acceptable range of respiration measures for the patient at rest. If the answer to the determination at step 316 is yes, this is indicative of the patient's cardiopulmonary distress being greater than if the determinations at either of steps 310 or 314 is yes. If the answer to the determination at step 316 is no, then flow returns to step 306 and 307. Alternatively, if the answer to the determination at step 316 is no, flow can return to steps 302 and 303, which is what may occur in embodiments where the baseline measures determined at step 302 and 303 are updated over time.

Exemplary different types of actions that can be triggered at steps 310, 314 and 318 will now be explained. The first action that is triggered at step 310 can be a first alert that informs the patient and/or a medical personnel that the patient's PAP is abnormal for the patient. The second action that is triggered at step 314 can be a second alert that informs the patient and/or a medical personnel that the patient's respiration is abnormal for the patient. The third action that is triggered at step 318 can be a third alert that informs the patient and/or a medical personnel that both the patient's PAP is abnormal for the patient and the patient's respiration is abnormal for the patient. Additionally, or alternatively, the third action that is triggered at step 318 can include adjusting at least one pacing parameter that is used to deliver cardiac pacing therapy using a portion of the system that is implanted. Exemplary pacing parameters that can be adjusted include, but are not limited to, pacing rate, atrioventricular (AV) delay, interatrial conduction (AA) delay, interventricular conduction (VV) delay, intraventricular delay (e.g., LV1-LV2 delay), and/or LV pacing site(s).

The first action that is triggered at step 310 can additionally, or alternatively, include adjusting at least one pacing parameter that is used to deliver cardiac pacing therapy using a portion of the system that is implanted. The second action that is triggered at step 314 can additionally, or alternatively, include adjusting at least one pacing parameter that is used to deliver cardiac pacing therapy using a portion of the system that is implanted. Where at least one pacing parameter is adjusted in each of steps 310, 314 and 316, the pacing parameter that is adjusted at the different steps 310, 314 and 316 differ from one another, and/or the specific adjustment made the a common pacing parameter at the different steps 310, 314 and 316 differ from one another.

In certain embodiments, at step 303, the second implantable sensor is used to determine a separate baseline measure of respiration for the patient at rest for each of a plurality of (i.e., at least two) different types of measures of respiration. In such embodiments, at step 305 an acceptable range of respiration measures for the patient at rest is determined for each of the plurality of different types of measures of respiration based on the respective baseline measure of respiration that is determined for the patient at rest. In certain embodiments, at one or more of steps 308, 312, and/or 316, the patient's respiration at rest is determined to be outside the acceptable range of respiration measures for the patient at rest whenever N out of M of the different types of measures of respiration is/are outside their respective baseline measure of respiration for the patient at rest, where M is a number specifying the different types of measures of respiration for which a respective acceptable range of respiration measures is determined for the patient at rest, and N is a predefined number that is equal to or less than M. For example, M can equal 3, and N can equal 2 or 3; or M can equal 4, and N can equal 2, 3 or 4. These are just a few examples, which are not intended to be all encompassing.

As part of steps 302 and 303, an implantable sensor, which may or may not be the same as one of the first and second implantable sensors, can be used to determine when the patient is at rest. In certain embodiments, the implantable sensor that is used to determine when the patient is at rest is an accelerometer, which is different than the first and second implantable sensors. Such an accelerometer can be an implementation of the activity/position sensor 272 discussed above with reference to FIG. 2. It would also be possible to detect whether a patient is at rest based on the sensed thoracic impedance signal and/or one or more other sensed signals.

In accordance with certain embodiments, the baseline measures determined at steps 302 and 303 can be determined at one point in time, and not updated thereafter. Alternatively, the baseline measures determined at steps 302 and 303 can be updated over time. For example, newly acquired data obtained from the first and second sensors can be used to determine a short term average for each measure of interest, e.g., by averaging the data over a relatively short period (e.g., every two minutes) and storing each short term average in a rolling buffer, or the like. The baseline measure of each measure of interest can be, e.g., a long term collected baseline that is averaged data over a relatively long period (e.g., four hours) that us updated every short period (e.g., two minutes) from the relevant short term average. For a more specific example, a baseline measure of PAP determined at step 302 can be an average of PAP measures collected over a four hour period, which average is updated every two minutes. Continuating with this example, the measure of the patient's PAP determined at each instance of step 306 can be an average of the patient's PAP over the most recent two minute period.

In certain embodiments, after an action is triggered at one of steps 310, 314, or 318, flow returns to step 306 and 307. Alternatively, flow can return to steps 302 and 303, which is what may occur in embodiments where the baseline measures determined at step 302 and 303 are updated over time.

In the flow diagram of FIG. 3, steps 302 and 303 are shown as being performed at the same time, as are steps 304 and 305, and steps 306 and 307. However, that need not be the case. In other words, the order of various steps shown in FIG. 3 can be changed while still being within the scope of the embodiments of the present technology. For another example, the order of steps 308, 312, and 316 can be changed. More generally, the order of many of the various steps shown in FIG. 3 may be changed.

A benefit of determining baseline measures at steps 302 and 303 while the patient is at rest is that such baseline measures should have low noise, and thus, should have a relatively high signal to noise ratio (SNR). A benefit of monitoring the patient's PAP and respiration at steps 306 and 307 while the patient is at rest is also that such measures should have low noise. Additionally, monitoring the patient's PAP and respiration at steps 306 and 307 while the patient is at rest reduces the probability that changes to the patient's PAP and/or respiration beyond respective acceptable ranges is/are caused by an underlying change in the patient's cardiopulmonary distress, rather than being temporarily caused by a temporary increase in patient motion or exercise.

Embodiments of the present technology described herein can be used, for example, to monitor and help treat patients that have the potential to develop decompensation and have been classified as NYHA Class I-IV, and thus, are indicated for receiving a CRD or other IMD.

Figure 4:
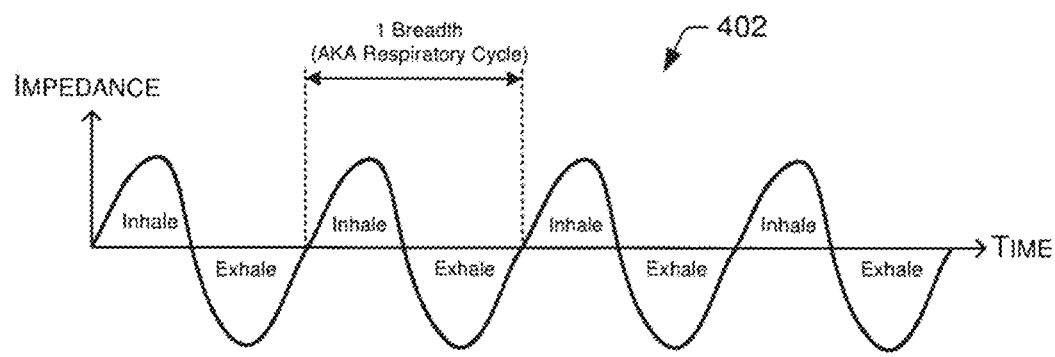
FIG. 4 illustrates an exemplary thoracis impedance signal.

FIG. 4 illustrates an exemplary thoracis impedance signal 402 obtained using the impedance measurement and processing circuitry 278. In accordance with certain embodiments, the baseline measure(s) or respiration for a patient at rest, which are determined at step 303, are determined from a thoracis impedance signal, similar to the signal 402 illustrated in FIG. 4. Exemplary baseline measures or respiration that can be determined from a thoracic impedance signal (e.g., 402) include, but are not limited to, respiration rate, tidal volume, inspiratory time, expiratory time, and minute ventilation. A measure indicative of respiration rate can be determined based on the temporal length of one breadth, which can also be referred to as one respiratory cycle. That measure can be left in terms of milliseconds or can be used to determine breadths per minute (bpm). Tidal volume is the lung volume representing the normal volume of air displaced between normal inhalation and exhalation when extra effort is not applied. In a healthy, young human adult, tidal volume is approximately 500 mL per inspiration or 7 mL/kg of body mass. A measure indicative of tidal volume can be determined by measuring the total area under the curve of a thoracic impedance signal during a respiratory cycle. Inspiratory time, which is the time taken for inhalation, can be determined, e.g., by measuring the length of time between zero crossings corresponding to a positive inflection in the thoracic impedance signal. Expiratory time, which is the time taken for exhalation, can be determined, e.g., by measuring the length of time between zero crossing corresponding to a negative inflection in the thoracic impedance signal. Minute ventilation (also known as "minute volume" or "respiratory minute volume") is the volume of gas inhaled (inhaled minute volume) or exhaled (exhaled minute volume) from a person's lungs per minute, or more specifically, the average respiratory rate per minute multiplied by the average tidal volume. A measure indicative of minute ventilation can be determined, e.g., by multiplying the average respiratory rate by the average total area under the curve of a cycle of the thoracic impedance signal. For a more specific example, where a patient's average tidal volume is 0.7 Liters per breath, and the patient's average respiration rate is 15 breaths per minute, then the patient's average minute ventilation would be 0.7×15=10.5 Liters per minute (L/min). Other ways of determining measures indicative of respiration rate, tidal volume, inspiratory time, expiratory time, and/or minute ventilation, based on a thoracic impedance signal, are also possible and within the scope of the embodiments described herein.

Figure 5:
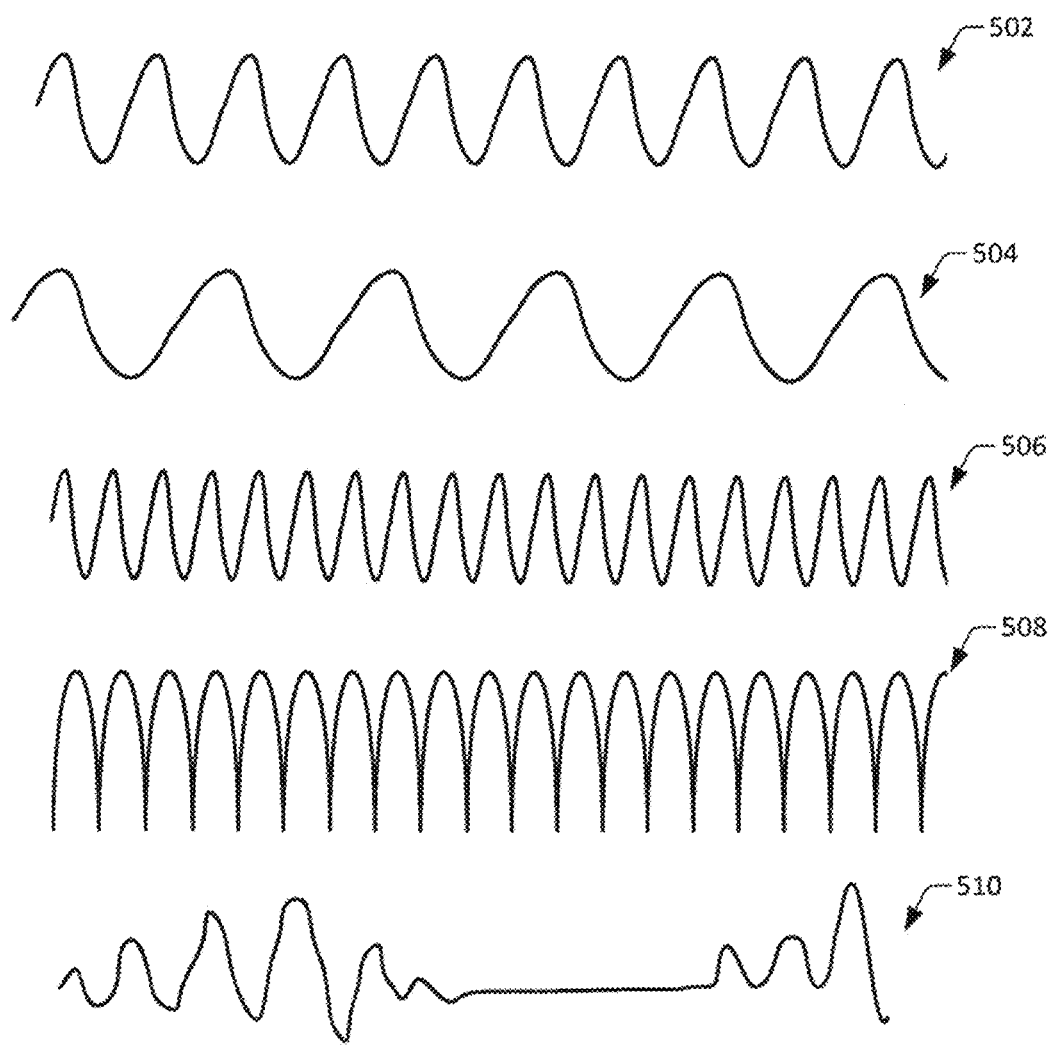
FIG. 5 illustrates exemplary thoracic impedance signals for various different respiratory or breathing states while a patient is at rest, including normal breathing, bradypnea, tachypnea, hyperventilation, and cheynes-strokes.

In accordance with certain embodiments of the present technology, various different types of respiration can be detected from a sensed thoracic impedance signal. For example, referring to FIG. 5, the thoracic impedance signal 502 corresponds to normal breathing in a resting state, the thoracic impedance signal 504 corresponds to bradypnea (i.e., a lower than normal respiratory rate), the thoracic impedance signal 506 corresponds to tachypnea (i.e., a higher than normal respiratory rate), the thoracic impedance signal 508 corresponds to hyperventilation (a condition where a person starts to breath very fast such that exhalation is greater than inhalation), and the thoracic impedance signal 510 corresponds to cheynes-strokes (i.e., an abnormal pattern of breathing characterized by progressively deeper, and sometimes faster, breathing followed by a gradual decrease that results in a temporary stop in breathing called an apnea). Through analysis of a sensed thoracis impedance signal, a system or device of an embodiment of the present technology can detect when the patient is breathing normally, as well as when the patient is experiencing bradypnea, tachypnea, hyperventilation, and/or cheynes-stokes. Such detections can be stored within an IMD and/or trigger alerts to medical personnel.

Exemplary details of a current pulse generator 604, which can be used to obtain a thoracic impedance signal, will now be described with reference to FIG. 6. Referring to FIG. 6, the current pulse generator 604 is shown as including two timing-controlled current generators 614 and 616 with programmable magnitude. The first current generator 614 sources current, the other current generator 616 sinks the current. As part of the charge and voltage balancing process, a switch SW Balance 618 is used to discharge an external capacitor Cap_Impulse 620 after each generated impulse. The pulse rate is programmable. Also shown in FIG. 6 is an exemplary triphasic pulse 605, generated by the current pulse generator 604 for application to the bodily tissue of a patient, and a corresponding sensed voltage waveform 607 that is sensed by the sensing circuit within the impedance measuring and processing circuitry 278 in FIG. 2.

The pulse waveform 605 possesses many special waveform features and electrical characteristics that are well suited for probing and measuring many types of physiological parameters in the body using current modulated or voltage modulated pulses. Additional details of such waveforms are described, as introduced above, in U.S. Pat. No. 8,010,196 to Wong et al, entitled "Tissue Characterization Using Intracardiac Impedances with an Implantable Lead System," issued Aug. 30, 2011, and incorporated herein by reference in its entirety. Exemplary waveform 605 is multiphasic, with a negative phase (the pulse segment below baseline) that balance a positive phase (the pulse segment above baseline). The illustrated waveform 605 is tri-phasic. Other versions of the waveform 605 may have more than three phases, may be synchronous or asynchronous, may be rectangular or sinusoidal, etc. One version of the waveform 605 uses the sinc(x) sampling waveform. In one variation, the exemplary impedance measurement architecture applies the waveform 605 as a voltage waveform instead of a current waveform and senses the results as electrical current instead of voltage.

Properties of the exemplary waveforms 605 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

The exemplary waveform 605 provides an elegant and reliable vehicle for measuring bodily impedances in a manner that gives reliably reproducible results. Instead of a conventional technique of trying to sense an instantaneous "snapshot" measurement of a conventionally injected signal, the impedance measurement and processing circuitry 278 can derive an impedance measurement by dividing the area under the sensed voltage curve (waveform 607) by the area of the injected current waveform 605. An exemplary implantable device 100 (discussed below) can perform this exemplary method by "integrating the curve" of an absolute value of waveforms 605 or 607. Sometimes the exemplary implantable device can closely approximate this integration without having to perform an integration operation by directly measuring and summing the area "under" the curve (e.g., under the rectangular wave) of the waveform 605, that is, the area composed of the absolute value of the three areas of the three phases of an exemplary tri-phasic waveform 605.

Likewise, the exemplary implantable device can integrate, or closely approximate the integration, by measuring and summing the area "under" the curve (e.g., the rectangular wave) of the waveform 607, that is, the area composed of the absolute value of the three areas of the three phases. In one implementation, the area of the sensed voltage, waveform 607, is measured at the output of an integrator circuit. The area of the injected current, waveform 605, is computed by, or preset by, the micro-controller driving the implantable device. An implantable device 100, discussed below with reference to FIGS. 1 and 2, may thus use this area-based ("areal") approach to deriving a network of impedance measurements over a multi-vector network 150. Additional details of the exemplary waveforms 605 and 607, and their benefits, can be appreciated from the '196 patent that was incorporated herein by reference above.

In the above description, the pulse generator 604 was described as being a current pulse generator that produces current pulses, and a sensing circuit 320 was described as being used to sense voltage signals indicative of impedances associated with selected sensing vectors. In alternative embodiments, a voltage pulse generator that produces voltage pulses can be used in place of the current pulse generator, in which case the sensing circuit would be configured to sense current signals indicative of impedance. The sensed current signals can then be converted to impedance signals using well known techniques, either before or after analog-to-digital conversions. While such alternative embodiments are also within the scope of the present invention, for consistency, the remainder of this description will typically focus on the electrical pulses being current pulses, and on the sensed signals being voltage signals.

In accordance with certain embodiments of the present technology, morphological changes with breathing disorders and heart failure decompensation can provide insight to the distress of a patient even when the respiratory rate may not rise significantly from a normal resting state. For example, a normal respiratory rate can be 12-16 breaths per minute, and a significant rise in respiratory rate can be an increase of 4 to 6 breaths/minute. There may however be an observed change in how the patient breathes. This change can be detected by using an algorithm in IMD hardware/firm ware/software that evaluates the rate of inspiratory time to expiratory time through the evaluation of area under and above the curves of the zero crossings of a thoracic impedance signal (e.g., 402).

The morphological change can also be detected by having an IMD and/or external device analyze points along the area (below and above a baseline of a thoracic impedance signal) by building a "normal" template, storing that template, and using that template for comparative purposes at selected time intervals. For example, once it has been established that the patient is in a normal resting state (where the patient is not under distress), the template could be generated over a 5 minute period, or some other length of time. That template could be stored (e.g., in memory 260) and then used by the IMD to compare to a newly generated respiratory waveform (e.g., thoracic impedance signal) at selected time intervals (e.g., during a resting state) or when a current generated waveform falls outside a specified deviation. This comparison can be used to provide an alert that the patient is under respiratory distress having either a restrictive or resistive ventilator pattern. Appropriate device parameters may be automatically changed in an IMD adapted to meet the physiological need, and/or an alert could be sent to a caring physician. The resting state can be determined by the change in minute ventilation, and/or using an accelerometer that is incorporated in the IMD.

In the above described embodiments, baseline measures of PAP and respiration were described as being determined for a patient at rest, with such baseline measures described as being used to determine an acceptable range of PAP measures for the patient at rest, and an acceptable range of respiration measures for the patient at rest. Further, measures of PAP and respiration were described as being monitored when the patient is at rest to see if one or both measures go outside their respective acceptable ranges in order to trigger various different actions (e.g., at steps 310, 314, and 318). In further embodiments, baseline measures of PAP and respiration can additionally (or alternatively) be determined for the patient at one or more other levels of exertion (in addition to, or instead of, when the patient is at rest) as determined using an activity sensor (e.g., an accelerometer). Such baseline measures (for a specific level of exertion) can be used to determine an acceptable range of PAP and an acceptable range of respiration measures for the patient at each of one or more specific level(s) of exertion. Measures of PAP and respiration can be monitored to see if one or both measures go outside their respective acceptable ranges, for a specific level or exertion, in order to trigger various different actions, similar to the different actions discussed above with reference to steps 310, 314, and 318. Levels of exertion, as determined from an accelerometer or other activity sensor, can be, e.g., in terms of raw sensor measurements, or in terms of a patient's steps per minute or walking speed in terms of miles per hour, but are not limited thereto.

Certain embodiments of the present technology described herein combine the monitoring of one or more respiration components (e.g., respiratory rate, tidal volume, inspiratory and/or expiratory time) in combination with PAP monitoring. Expected benefits of combining these types of monitoring include improvements to the early detection of changes in a patient's status and an improved ability to change the pacing parameters and/or configurations to meet the patients changing conditions. This may include notification to the health care provider, modification of the pacing parameters that include, but are not limited to, pacing mode, atrial to ventricular delays, rate response ventricular to ventricular timing, selection of the pacing lead configuration. The combination of the change in PAP and the associated change in one or more respiratory parameter should lead to an early detection or improvement of the patient. The change in the parameters would also signal a change that could be monitored by the IMD to change the pacing configuration automatically, as well as simultaneously notifying a health care provider of the change in the monitored parameters and the IMD changes.

In accordance with certain embodiments, the type of cardiopulmonary distress that a patient is experiencing can be determined based on the morphology or other characteristics of a sensed thoracic impedance signal. Exemplary types of cardiopulmonary distress that may be detected included, but are not limited to, dyspnea, orthopnea, and paroxysmal nocturnal dyspnea. The severity of such various types of cardiopulmonary distress can be determined based on the thoracic impedance signal alone, or more preferably, also based on one or more measures of PAP. For example, where a specific type of cardiopulmonary distress is occurring while the patient's PAP is within its acceptable range can be considered less severe than if the patient's PAP is outside its acceptable range.

It is understood that the present subject matter may be embodied in many different forms and should not be construed as being limited to the embodiments set forth herein. Rather, these embodiments are provided so that this subject matter will be thorough and complete and will fully convey the disclosure to those skilled in the art. Indeed, the subject matter is intended to cover alternatives, modifications and equivalents of these embodiments, which are included within the scope and spirit of the subject matter as defined by the appended claims. Furthermore, in the following detailed description of the present subject matter, numerous specific details are set forth in order to provide a thorough understanding of the present subject matter. However, it will be clear to those of ordinary skill in the art that the present subject matter may be practiced without such specific details.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

The disclosure has been described in conjunction with various embodiments. However, other variations and modifications to the disclosed embodiments can be understood and effected from a study of the drawings, the disclosure, and the appended claims, and such variations and modifications are to be interpreted as being encompassed by the appended claims. In the claims, the word "comprising" does not exclude other elements or steps, and the indefinite article "a" or "an" does not exclude a plurality.

For purposes of this document, it should be noted that the dimensions of the various features depicted in the figures may not necessarily be drawn to scale.

For purposes of this document, reference in the specification to "an embodiment," "one embodiment," "some embodiments," or "another embodiment" may be used to describe different embodiments or the same embodiment.

For purposes of this document, a connection may be a direct connection or an indirect connection (e.g., via one or more other parts). In some cases, when an element is referred to as being connected or coupled to another element, the element may be directly connected to the other element or indirectly connected to the other element via intervening elements. When an element is referred to as being directly connected to another element, then there are no intervening elements between the element and the other element. Two devices are "in communication" if they are directly or indirectly connected so that they can communicate electronic signals between them.

For purposes of this document, the term "based on" may be read as "based at least in part on."

For purposes of this document, without additional context, use of numerical terms such as a "first" object, a "second" object, and a "third" object may not imply an ordering of objects, but may instead be used for identification purposes to identify different objects. For example, the terms "first" sensor and "second" sensor do not imply an ordering of the sensors, but instead, are used to identify different sensors.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. It is intended that the scope be defined by the claims appended hereto.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for use by a system at least a portion of which is implanted within a patient and used to deliver cardiac pacing therapy, the method comprising:
   using a first implantable sensor to determine a baseline measure of pulmonary arterial pressure (PAP) for the patient at rest;
   using a second implantable sensor to determine a baseline measure of respiration for the patient at rest;
   determining an acceptable range of PAP measures for the patient at rest based on the baseline measure of PAP that is determined for the patient at rest;
   determining an acceptable range of respiration measures for the patient at rest based on the baseline measure of respiration that is determined for the patient at rest;
   using the first implantable sensor to detect whenever the patient's PAP at rest is outside the acceptable range of PAP measures for the patient at rest;
   using the second implantable sensor to detect whenever the patient's respiration at rest is outside the acceptable range of respiration measures for the patient at rest;
   triggering a first action in response to detecting that the patient's PAP at rest is outside the acceptable range of PAP measures for the patient at rest, while contemporaneously the patient's respiration at rest is within the acceptable range of respiration measures for the patient at rest;
   triggering a second action in response to detecting that the patient's respiration at rest is outside the acceptable range of respiration measures for the patient at rest, while contemporaneously the patient's PAP at rest is within the acceptable range of PAP measures for the patient at rest; and
   triggering a third action in response to detecting that the patient's PAP at rest is outside the acceptable range of PAP measures for the patient at rest, while contemporaneously the patient's respiration at rest is outside the acceptable range of respiration measures for the patient at rest, the third action comprising adjusting a pacing parameter that is used for the cardiac pacing therapy and is selected from a group consisting of a pacing rate, an atrio-ventricular (AV) delay, an interatrial conduction (AA) delay, an interventricular conduction (VV) delay, an intraventricular (LV1-LV2) delay, and an LV pacing site;
   wherein the first, second, and third actions differ from one another.

2. The method of claim 1, wherein:
   the first action that is triggered comprises a first alert that informs at least one of the patient or a medical personnel that the patient's PAP is abnormal for the patient;
   the second action that is triggered comprises a second alert that informs at least one of the patient or a medical personnel that the patient's respiration is abnormal for the patient; and
   the third action that is triggered also comprises a third alert that informs at least one of the patient or a medical personnel that both the patient's PAP is abnormal for the patient and the patient's respiration is abnormal for the patient.

3. The method of claim 1, wherein:
   the second action that is triggered also comprises adjusting a pacing parameter that is used for cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
   the pacing parameter that is adjusted and corresponds to the second action differs from the pacing parameter that is adjusted and corresponds to the third action.

4. The method of claim 1, wherein the baseline measure of respiration for the patient at rest is selected from the group consisting of:
   a baseline measure indicative of respiration rate for the patient at rest;
   a baseline measure indicative of tidal volume for the patient at rest;
   a baseline measure indicative of inspiratory time for the patient at rest;
   a baseline measure indicative of expiratory time for the patient at rest;
   a baseline measure indicative of minute ventilation for the patient at rest; and
   a baseline measure indicative of morphology of a signal waveform indicative of respiration for the patient at rest.

5. The method of claim 1, wherein:
   the second implantable sensor is used to determine a separate baseline measure of respiration for the patient at rest for each of a plurality of different types of measures of respiration;
   an acceptable range of respiration measures for the patient at rest is determined for each of the plurality of different types of measures of respiration based on the respective baseline measure of respiration that is determined for the patient at rest; and the patient's respiration at rest is determined to be outside the acceptable range of respiration measures for the patient at rest whenever N out of M of the different types of measures of respiration is/are outside their respective baseline measure of respiration for the patient at rest, where M is a number specifying the different types of measures of respiration for which a respective acceptable range of respiration measures is determined for the patient at rest, and N is a predefined number that is equal to or less than M.

6. The method of claim 5, wherein a said acceptable range of respiration measures for the patient at rest is determined for at least two of the following different types of measures of respiration:
respiration rate for the patient at rest;
tidal volume for the patient at rest;
inspiratory time for the patient at rest;
expiratory time for the patient at rest;
minute ventilation for the patient at rest; or
morphology of a signal waveform indicative of respiration for the patient at rest.

7. The method of claim 1, further comprising:
using an implantable sensor, which may or may not be the same as one of the first and second implantable sensors, to determine when the patient is at rest.

8. The method of claim 7, wherein:
the implantable sensor that is used to determine when the patient is at rest comprises an accelerometer, which is different than the first and second implantable sensors.

9. The method of claim 1, wherein:
the first implantable sensor is configured to sense PAP; and
the second implantable sensor is configured to sense thoracic impedance.

10. The method of claim 9, wherein:
the second implantable sensor is configured to produce a thoracic impedance signal from which one or more types of respiration measures can be determined.

11. The method of claim 1, wherein:
each of the first, second, and third actions comprise adjusting a same pacing parameter that is used for the cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
adjustments that are made to the same pacing parameter and correspond to the first, second, and third actions differ from one another.

12. A system at least a portion of which is implantable within a patient, the system comprising:
a first implantable sensor configured to sense pulmonary arterial pressure (PAP);
a second implantable sensor configured to sense thoracic impedance;
one or more processors configured to:
determine a baseline measure of PAP for the patient at rest based on one or more measures obtained using the first implantable sensor;
determine a baseline measure of respiration for the patient at rest based on one or more measures obtained using the second implantable sensor;
determine an acceptable range of PAP measures for the patient at rest based on the baseline measure of PAP that is determined for the patient at rest;
determine an acceptable range of respiration measures for the patient at rest based on the baseline measure of respiration that is determined for the patient at rest;
detect whenever the patient's PAP at rest is outside the acceptable range of PAP measures for the patient at rest based on one or more measures obtained using the first implantable sensor;
detect whenever the patient's respiration at rest is outside the acceptable range of respiration measures for the patient at rest based on one or more measures obtained using the second implantable sensor;
trigger a first action in response to a detection that the patient's PAP at rest is outside the acceptable range of PAP measures for the patient at rest, while contemporaneously the patient's respiration at rest is within the acceptable range of respiration measures for the patient at rest;
trigger a second action in response to a detection that the patient's respiration at rest is outside the acceptable range of respiration measures for the patient at rest, while contemporaneously the patient's PAP at rest is within the acceptable range of PAP measures for the patient at rest; and
trigger a third action in response to a detection that the patient's PAP at rest is outside the acceptable range of PAP measures for the patient at rest, while contemporaneously the patient's respiration at rest is outside the acceptable range of respiration measures for the patient at rest, the third action comprising adjusting a pacing parameter that is used for the cardiac pacing therapy and is selected from a group consisting of a pacing rate, an atrio-ventricular (AV) delay, an interatrial conduction (AA) delay, an interventricular conduction (VV) delay, an intraventricular (LV1-LV2) delay, and an LV pacing site;
wherein the first, second, and third actions differ from one another.

13. The system of claim 12, wherein:
the first action that is triggered comprises a first alert that informs at least one of the patient or a medical personnel that the patient's PAP is abnormal for the patient;
the second action that is triggered comprises a second alert that informs at least one of the patient or a medical personnel that the patient's respiration is abnormal for the patient; and
the third action that is triggered also comprises a third alert that informs at least one of the patient or a medical personnel that both the patient's PAP is abnormal for the patient and the patient's respiration is abnormal for the patient.

14. The system of claim 12, wherein:
the second action that is triggered also comprises adjusting a pacing parameter that is used for cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
the pacing parameter that is adjusted and corresponds to the second action differs from the pacing parameter that is adjusted and corresponds to the third action.

15. The system of claim 12, wherein the one or more processors is/are configured to:
determine a separate baseline measure of respiration for the patient at rest for each of a plurality of different types of measures of respiration;

determine an acceptable range of respiration measures for the patient at rest for each of the plurality of different types of measures of respiration based on the respective baseline measure of respiration that is determined for the patient at rest; and determine that the patient's respiration at rest is outside the acceptable range of respiration measures for the patient at rest whenever N out of M of the different types of measures of respiration is/are outside their respective baseline measure of respiration for the patient at rest;

where M is a number specifying the different types of measures of respiration for which a respective acceptable range of respiration measures is determined for the patient at rest, and N is a predefined number that is equal to or less than M.

16. The system of claim 12, wherein the one or more processors is/are configured to use an implantable sensor, which may or may not be the same as one of the first or second implantable sensors, to determine when the patient is at rest.

17. The system of claim 16, wherein the implantable sensor that is used to determine when the patient is at rest comprises an accelerometer, which is different than the first and second implantable sensors.

18. The system of claim 12, wherein:
the second implantable sensor is configured to produce a thoracic impedance signal from which one or more types of respiration measures can be determined.

19. The method of claim 1, wherein:
each of the first, second, and third actions comprises adjusting a pacing parameter that is used for the cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
the pacing parameters that are adjusted and correspond to the first, second, and third actions differ from one another.

20. The system of claim 12, wherein:
each of the first, second, and third actions comprises adjusting a pacing parameter that is used for the cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
the pacing parameters that are adjusted and correspond to the first, second, and third actions differ from one another.

21. The system of claim 12, wherein:
each of the first, second, and third actions comprise adjusting a same pacing parameter that is used for the cardiac pacing therapy and is selected from the group consisting of a pacing rate, an atrio-ventricular (AV) delay, an interatrial conduction (AA) delay, an interventricular conduction (VV) delay, an intraventricular (LV1-LV2) delay, and an LV pacing site; and
adjustments that are made to the same pacing parameter and correspond to the first, second, and third actions differ from one another.

22. A method for use by a system at least a portion of which is implanted within a patient, the method comprising:
sensing pulmonary arterial pressure (PAP) and thoracic impedance of a patient;
detecting, based on the sensed PAP, whenever the patient's PAP is outside an acceptable range of PAP measures for the patient;
detecting, based on the sensed thoracic impedance, whenever the patient's respiration is outside an acceptable range of respiration measures for the patient;
triggering a first action in response to detecting that the patient's PAP is outside the acceptable range of PAP measures for the patient, while contemporaneously the patient's respiration is within the acceptable range of respiration measures for the patient;
triggering a second action in response to detecting that the patient's respiration is outside the acceptable range of respiration measures for the patient, while contemporaneously the patient's PAP is within the acceptable range of PAP measures for the patient; and
triggering a third action in response to detecting that the patient's PAP is outside the acceptable range of PAP measures for the patient, while contemporaneously the patient's respiration is outside the acceptable range of respiration measures for the patient;
wherein each of the first, second, and third actions comprises adjusting a pacing parameter that is used for the cardiac pacing therapy and is selected from a group consisting of a pacing rate, an atrio-ventricular (AV) delay, an interatrial conduction (AA) delay, an interventricular conduction (VV) delay, an intraventricular (LV1-LV2) delay, and an LV pacing site; and
wherein the pacing parameters that are adjusted and correspond to the first, second, and third actions differ from one another.

23. The method of claim 22, wherein:
the first action that is triggered comprises a first alert that informs at least one of the patient or a medical personnel that the patient's PAP is abnormal for the patient;
the second action that is triggered comprises a second alert that informs at least one of the patient or a medical personnel that the patient's respiration is abnormal for the patient; and
the third action that is triggered comprises adjusting at least one pacing parameter that is used to deliver cardiac pacing therapy using a portion of the system that is implanted.

* * * * *